(12) United States Patent
Wu

(10) Patent No.: US 11,439,404 B2
(45) Date of Patent: Sep. 13, 2022

(54) INDWELLING DEVICE FOR EMBOLIZATION AND METHOD FOR MANUFACTURING THE SAME

(71) Applicant: KANEKA CORPORATION, Osaka (JP)

(72) Inventor: Qian Wu, Settsu (JP)

(73) Assignee: KANEKA CORPORATION, Osaka (JP)

( * ) Notice: Subject to any disclaimer, the term of this patent is extended or adjusted under 35 U.S.C. 154(b) by 167 days.

(21) Appl. No.: 16/642,249

(22) PCT Filed: Jul. 27, 2018

(86) PCT No.: PCT/JP2018/028265
§ 371 (c)(1),
(2) Date: Feb. 26, 2020

(87) PCT Pub. No.: WO2019/054065
PCT Pub. Date: Mar. 21, 2019

(65) Prior Publication Data
US 2020/0352576 A1 Nov. 12, 2020

(30) Foreign Application Priority Data
Sep. 12, 2017 (JP) .............................. JP2017-174746

(51) Int. Cl.
*A61B 17/12* (2006.01)
*A61B 17/00* (2006.01)

(52) U.S. Cl.
CPC .. *A61B 17/12154* (2013.01); *A61B 17/12113* (2013.01); *A61B 2017/00526* (2013.01);
(Continued)

(58) Field of Classification Search
CPC ...... A61B 17/12154; A61B 2017/1205; A61B 2017/12068; A61B 2017/12072;
(Continued)

(56) References Cited

U.S. PATENT DOCUMENTS 6,776,788 B1 8/2004 Klint et al.
2004/0002731 A1 1/2004 Aganon et al.
(Continued)

FOREIGN PATENT DOCUMENTS

JP 2000-517222 A 12/2000
JP 2005-530591 A 10/2005
(Continued)

OTHER PUBLICATIONS

International Search Report (PCT/ISA/210) issued in PCT/JP2018/028265, dated Aug. 28, 2018.
(Continued)

*Primary Examiner* — Katherine H Schwiker
*Assistant Examiner* — Raihan R Khandker
(74) *Attorney, Agent, or Firm* — Birch, Stewart, Kolasch & Birch, LLP

(57) ABSTRACT

An indwelling device for embolization comprises a coil portion (11) having a proximal side and a distal side and having a lumen extending in a longitudinal direction, a stretch-resistant member (20) disposed in the lumen, wherein the indwelling device has a fixing structure in which the stretch-resistant member (20) is knotted to the detachable portion attached in the lumen of a proximal end part of the coil portion (11) and extending proximally from a proximal end of the lumen, in order for the stretch-resistant member (20) to be more securely anchored to the coil portion (11).

18 Claims, 4 Drawing Sheets

(52) U.S. Cl.
CPC .......... *A61B 2017/00867* (2013.01); *A61B 2017/1205* (2013.01); *A61B 2017/12068* (2013.01)

(58) Field of Classification Search
CPC ...... A61B 2017/00526; A61B 17/1214; A61B 17/12145; A61B 17/1215; A61B 17/12168; A61B 17/12172; A61B 17/1217; A61B 17/1205; A61B 17/12022; A61B 17/12113; A61B 17/12118; A61B 17/12109; A61B 17/0057; A61B 2017/12054–12095; A61B 2017/00623; A61F 2/011
See application file for complete search history.

(56) References Cited

U.S. PATENT DOCUMENTS

| | | | |
|---|---|---|---|
| 2004/0002732 A1 | 1/2004 | Teoh et al. | |
| 2004/0002733 A1 | 1/2004 | Teoh | |
| 2004/0186491 A1 | 9/2004 | Klint et al. | |
| 2005/0267494 A1 | 12/2005 | Iwata et al. | |
| 2007/0112375 A1 | 5/2007 | Aganon et al. | |
| 2008/0046093 A1 | 2/2008 | Davis | |
| 2008/0228215 A1* | 9/2008 | Strauss | A61B 17/12154 606/191 |
| 2009/0062812 A1 | 3/2009 | Fitz et al. | |
| 2009/0254111 A1 | 10/2009 | Monstadt et al. | |
| 2010/0331948 A1* | 12/2010 | Turovskiy | A61F 2/95 623/1.11 |
| 2011/0213406 A1 | 9/2011 | Aganon et al. | |
| 2012/0172921 A1 | 7/2012 | Yamanaka et al. | |
| 2012/0209310 A1* | 8/2012 | Chen | A61B 17/12022 606/195 |
| 2014/0277084 A1 | 9/2014 | Mirigian et al. | |
| 2014/0277085 A1 | 9/2014 | Mirigian et al. | |
| 2014/0277092 A1 | 9/2014 | Teoh et al. | |
| 2016/0206322 A1 | 7/2016 | Fitz et al. | |
| 2017/0354418 A1 | 12/2017 | Teoh et al. | |
| 2018/0028190 A1 | 2/2018 | Ozasa et al. | |
| 2018/0271533 A1* | 9/2018 | Le | A61B 17/12022 |
| 2018/0353188 A1 | 12/2018 | Fitz et al. | |

FOREIGN PATENT DOCUMENTS

| | | |
|---|---|---|
| JP | 2008-538952 A | 11/2008 |
| JP | 2015-128677 A | 7/2015 |
| JP | 2016-511065 A | 4/2016 |
| JP | 2016-512085 A | 4/2016 |
| JP | 2016-154946 A | 9/2016 |
| WO | WO 2016/140314 A1 | 9/2016 |

OTHER PUBLICATIONS

International Search Report (PCT/ISA/210) issued in PCT/JP2018/028266, dated Aug. 28, 2018.

Written Opinion of the International Searching Authority (PCT/ISA/237) issued in PCT/JP2018/028265, dated Aug. 28, 2018.

Written Opinion of the International Searching Authority (PCT/ISA/237) issued in PCT/JP2018/028266, dated Aug. 28, 2018.

\* cited by examiner

[Fig. 7]
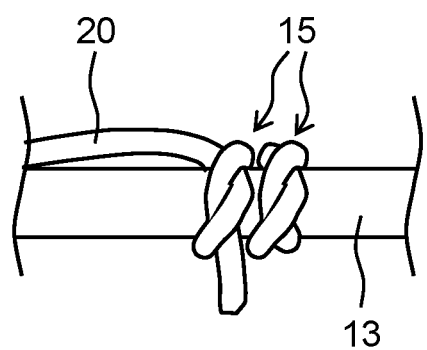

INDWELLING DEVICE FOR EMBOLIZATION AND METHOD FOR MANUFACTURING THE SAME

TECHNICAL FIELD

The present invention relates to an indwelling device for embolization, and particularly to an indwelling device for embolization used for embolization of a lesioned part such as an aneurysm.

BACKGROUND ART

Currently, an endovascular treatment method using a catheter or the like is known as a less invasive treatment method for an intravascular lesion such as an aneurysm. In the endovascular treatment, there is a method of, for example, inserting an indwelling device for embolization (hereinafter simply referred to as an "indwelling device") into an aneurysm through a catheter, placing a part of the indwelling device by cutting off at a detachable portion, and embolizing the aneurysm. A part of the indwelling device placed in the aneurysm becomes a physical obstacle to a blood flow and a thrombus is formed around the part of the indwelling device, whereby a risk of rupture of the aneurysm can be reduced.

An indwelling device has a structure in which a coil portion to be placed in a body and a pusher portion for delivering the coil portion to a predetermined site are connected via a detachable portion. The coil portion is placed at a predetermined site such as an aneurysm, followed by cutting the detachable portion by mechanical, thermal or electrical operation.

The indwelling device is required to have a function so that the coil portion is prevented or suppressed from stretching unlimitedly, in order to reliably perform a repositioning operation that corrects an indwelling state by recovering the coil portion into a catheter after the coil portion pushed out from the catheter is placed at a predetermined site and before cutting.

As a means for preventing or suppressing stretch of the coil portion, a method of anchoring a stretch-resistant member, which can suppress the stretch of the coil portion in its axial direction, to both ends inside the coil portion, is employed. The stretch-resistant member is required to have high strength for the reason described above. Accordingly, in order to enhance safety more during the operation, the stretch-resistant member is preferably made of a material having relatively high strength such as, for example, a precious metal and a resin polymer (e.g., polypropylene or polyethylene).

The stretch-resistant member is anchored to a proximal end part and a distal end part of the coil portion. As an anchoring method thereof, a method of adhesion, welding, crimping or physically connecting of the stretch-resistant member to both end parts of the coil portion is often used. In order to ensure the function of preventing or suppressing stretch of the coil portion of the stretch-resistant member, it is preferable to anchor the stretch-resistant member to both ends of the coil portion. Though the stretch-resistant function can be ensured by a conventional method such as adhesion, welding, pressure bonding and physically connecting, a more stable stretch-resistant function can be realized by further enhancing anchoring strength to the coil portion.

Patent Literature 1 discloses an indwelling device in which a detaching suture extending in a coil portion of a primary coil passes through a head of a delivery pusher, a loop of a coil hook and a front opening of a blade, and is anchored to an inner shaft by a suture locking tube. Patent Literature 1 also discloses that a proximal end of the suture may be tied into a knot around an inner shaft and adhesive may be applied to the knot, or the knot may be slightly melted to further secure the suture in position. In the device according to Patent Literature 1, the coil portion is placed at a predetermined site by cutting the suture. However, in the configuration disclosed in Patent Literature 1, since the suture is not anchored to both ends of the coil portion, when the suture is cut by the blade, the stretch-resistant effect to the coil portion may be lost.

Patent Literature 2 discloses a vaso-occlusive device delivery assembly comprising a pusher assembly having proximal and distal ends, a conductive sacrificial link disposed at a distal end of the pusher assembly, and a vaso-occlusive device secured to the pusher assembly by the sacrificial link. In addition, it is also disclosed of the vaso-occlusive device delivery assembly, in which the vaso-occlusive device comprises a stretch-resisting member having a distal end secured to a distal portion of the vaso-occlusive device, wherein a distal end connector portion of the sacrificial link extends distally of the distal connector member, and is secured to a proximal end of the stretch-resisting member. The sacrificial link of Patent Literature 2 is electrically coupled between respective first and second conductors, such that the first conductor, the sacrificial link, and the second conductor form an electrical circuit, and when a disintegration current is applied to the first and second conductors through the sacrificial link, the sacrificial link is thermally disintegrated, thereby releasing the vaso-occlusive device from the pusher assembly. In the vaso-occlusive device according to Patent Literature 2, since the stretch-resisting member is not anchored by tying to both ends of the vaso-occlusive device, the stretch-resisting member may be detached from the conductor in moving the vaso-occlusive device in a catheter or during operations such as repositioning.

Patent Literature 3 discloses a detachable implant delivery system comprising a heater, a delivery device, an implant attached to a distal end of the delivery device, a stretch-resistant member connecting the delivery device and the implant, attached to two points inside the implant and a third point on the delivery relative device, wherein the stretch-resistant member is attached to the implant by a knot, and the stretch-resistant member near the third point close to the heater is broken upon activation of the heater, thereby releasing the implant. In the delivery system according to Patent Literature 3, the proximal ends of the stretch-resistant member attached to the two points inside the implant remain as free ends after detachment, and thus may be frayed out of the implant.

CITATION LIST

Patent Literature

Patent Literature 1
  Japanese Unexamined Laid-open Patent Application Publication No. 2016-511065
Patent Literature 2
  Japanese Unexamined Laid-open Patent Application Publication No. 2016-512085
Patent Literature 3
  Japanese Unexamined Laid-open Patent Application Publication No. 2016-154946

SUMMARY OF INVENTION

Technical Problem

In the case that the stretch-resistant member is not securely anchored to both ends of the coil portion, the coil portion is highly likely to extend unintentionally due to the stretch-resistant member coming off the coil portion. The stretched coil portion is difficult to be recovered and may damage a lesion. Therefore, there is a need for an indwelling device in which the stretch-resistant member can be securely anchored to the coil portion.

Solution to Problem

As a result of intensive studies for solving the above-mentioned problems, the present inventors have completed the present invention. That is, the present invention relates to the following indwelling device for embolization and manufacturing method thereof.

[1] An indwelling device for embolization comprising
a coil portion having a proximal side and a distal side and having a lumen extending in a longitudinal direction,
a stretch-resistant member disposed in the lumen,
a rod-shaped detachable portion attached in the lumen of a proximal end part of the coil portion and extending proximally from a proximal end of the lumen, and
a fixing structure in which the stretch-resistant member is knotted to the detachable portion.

[2] The indwelling device for embolization according to [1], wherein an insulating portion is disposed on the detachable portion and proximal to the fixing structure.

[3] The indwelling device for embolization according to [1] or [2], wherein the coil portions has a small diameter portion at a proximal end part, the small diameter portion has an inner diameter, which is smaller than an inner diameter of a distal part of the coil portion.

[4] The indwelling device for embolization according to any one of [1] to [3], wherein the fixing structure includes at least one half-knot disposed proximal to a proximal end of the lumen.

[5] The indwelling device for embolization according to any one of [1] to [4], wherein the fixing structure includes a plurality of half-knots located at different positions.

[6] The indwelling device for embolization according to any one of [1] to [5], wherein the stretch-resistant member is disposed in the lumen and is folded in a two-folded state at a distal part of the coil portion.

[7] The indwelling device for embolization according to any one of [1] to [6], wherein the fixing structure includes a cured adhesive, and the adhesive is selected from a group consisting of an ultraviolet curable adhesive, a thermosetting adhesive and a moisture curable adhesive each having a viscosity of 10 mPa·s to 2000 mPa·s.

[8] The indwelling device for embolization according to [7], wherein the cured adhesive is disposed to extend from a proximal part of the coil portion to a distal part of the detachable portion.

[9] The indwelling device for embolization according to any one of [1] to [8], wherein a distal end of the detachable portion is disposed inside the coil portion, and a knot of the stretch-resistant member is disposed out of the coil portion.

[10] The indwelling device for embolization according to any one of [1] to [9], wherein the detachable portion contains a heat-melt material.

[11] The indwelling device for embolization according to any one of [1] to [10], wherein the coil portion, the detachable portion and a pusher portion are disposed in this order from a distal side of the indwelling device, and the coil portion and the pusher portion are connected to each other via the detachable portion.

[12] A method for manufacturing an indwelling device for embolization comprising: disposing a stretch-resistant member inside a coil portion; inserting a detachable portion into a proximal end part of the coil portion; forming a fixing structure by knotting the stretch-resistant member to the detachable portion; injecting an adhesive into the fixing structure; and curing the adhesive.

[13] The method for manufacturing an indwelling device for embolization according to [12], further comprising reducing an inner diameter of a proximal end of the coil portion after the step of disposing the stretch-resistant member inside the coil portion.

Advantageous Effects of Invention

The indwelling device of the present invention has high anchoring strength between the stretch-resistant member and the coil portion.

BRIEF DESCRIPTION OF DRAWINGS

FIG. 7 shows an example of a fixing structure in which a stretch-resistant member is knotted to a detachable portion by two half-knots.

DESCRIPTION OF EMBODIMENTS

Figure 1:
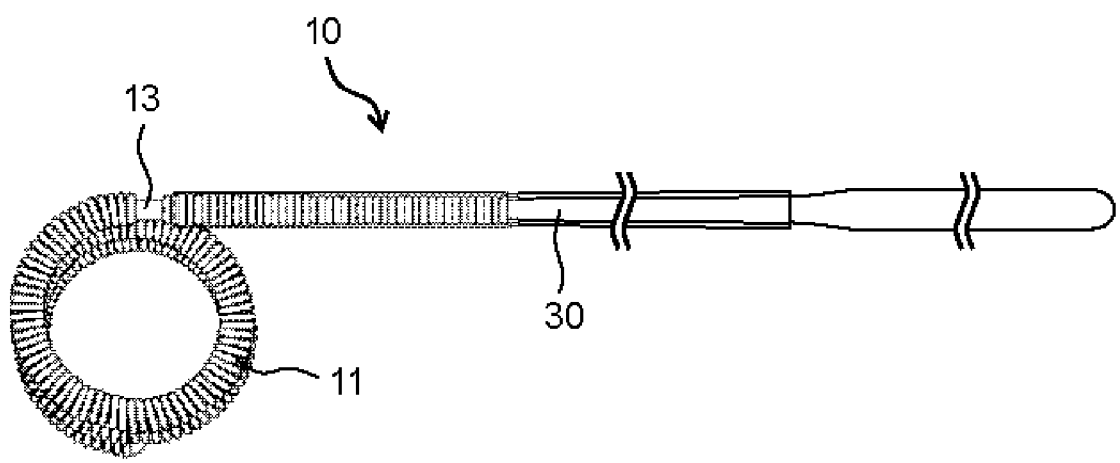
FIG. 1 shows an example of an indwelling device for embolization of the present invention and represents an overall lateral view of the indwelling device.

Hereinafter, the present invention will be specifically explained below based on the following embodiments; however, the present invention is not restricted by the embodiments described below of course, and can be certainly put into practice after appropriate modifications within in a range meeting the gist of the above and the below, all of which are included in the technical scope of the present invention. In the drawings, hatching or a reference sign for a member may be omitted for convenience, and in such a case, the description and other drawings should be referred to. In addition, sizes of various members in the drawings may differ from the actual sizes thereof, since priority is given to understanding the features of the present invention.

An indwelling device for embolization (hereinafter simply referred to as an "indwelling device") 10 of the present invention comprises a coil portion 11, a detachable portion 13 and a pusher portion 30 from a distal side thereof, as shown in FIG. 1. In the indwelling device 10, a head side of the coil portion 11 is referred to as a distal side, and a side opposite to the detachable portion 13 of the pusher portion 30 is referred to as a proximal side. A distal and proximal direction of the indwelling device 10 is referred to as a longitudinal direction. A proximal part and a distal part respectively mean a part on the proximal side and a part on the distal side from the center in the longitudinal direction in a target member, and preferably respectively means a one-third part on the proximal side and a one-third part on the distal side. A proximal end part means a part including the proximal end in a target member, for example, a one-eighth part on the proximal side, and a distal end part means a part including the distal end in a target member, for example, a one-eighth part on the distal side.

The indwelling device 10 comprises the coil portion 11 having a lumen extending in the longitudinal direction. The lumen is a cavity inside the coil. The lumen may extend over the entire length of the coil portion 11 or may have a structure in which a part of the coil lumen is closed. It is preferable that the indwelling device 10 comprises the coil portion 11, and a head part 12 having a substantially hemispherical round shape is disposed at a distal end part of the coil portion 11, that is, a left end part of the coil portion 11 in FIG. 2. The detachable portion 13 having, for example, a rod shape, that connects the coil portion 11 and the pusher portion 30 is disposed at a proximal end part of the coil portion 11. The detachable portion 13 is attached in the lumen of the proximal end part of the coil portion 11 and is disposed so as to extend proximally from the proximal end of the lumen. That is, the detachable portion 13 is disposed so as to protrude and extend proximally from a proximal end of the coil portion 11, that is, so as to protrude and extend toward a right side in FIG. 2, in the state where a part of a distal part thereof is attached to an inner surface of the proximal end part of the coil portion 11. A proximal part of the detachable portion 13 is attached to the pusher portion 30. In the indwelling device 10, the shape of the head part 12 is not limited to a substantially hemispherical round shape, and other shapes that do not damage a blood vessel can be adopted. The detachable portion 13 is a part that connects the coil portion 11 to any pusher or the like, and the coil portion 11 is detachably anchored to the pusher portion 30 via the detachable portion 13.

The coil portion 11 is generally configured by winding a metal wire in a spiral shape. Such a metal wire can be selected from among those that are chemically stable to a human body like noble metals, those that are chemically stabilized by forming a passive film on the surface in vivo, those that have low toxicity or those that are biocompatible when it is left in a human body for a long time. For example, platinum, gold, titanium, tungsten, alloys thereof, stainless steels and the like can be exemplified as the metal material. Among them, a platinum alloy such as platinum-tungsten is preferably used for the coil portion 11, since it has chemical stability in vivo, excellent physical properties such as strength and elasticity, and processability.

The coil portion 11 constituting the indwelling device 10 preferably has bendability or flexibility, and preferably has the following configuration, though it may vary depending on the material of the metal wire. A diameter of the metal wire constituting the coil portion 11, that is, a wire diameter is preferably 10 μm or larger and 120 μm or smaller. A coil diameter of the coil portion 11 is preferably 100 μm or larger and 500 μm or smaller. A coil length of the coil portion 11 is preferably 2 mm or longer and 500 mm or shorter.

The coil portion 11 may have a shape in which a metal wire is wound in a spiral shape, or it may be configured to have a coil shape in which a metal wire is wound in a spiral shape as a primary shape and have a secondary shape in which the primary shape is further formed into a certain shape. The metal wire can be formed into a coil-shaped primary shape by winding around a cylindrical primary mold. Further, the coil having the primary shape can be wound around a cylindrical secondary mold to give a coil-shaped secondary shape. Alternatively, the coil having the primary shape can be inserted into a predetermined box-shaped secondary mold to give a box-shaped secondary shape. The metal wire, the primary shape or the like can be imparted a certain shape by winding around a mold or inserting into a mold, followed by heating. After imparting the secondary shape to the coil portion 11, a tertiary shape can be further imparted. As the mold, a mold in which a wire or a coil is wound on its outside to impart a shape, or a mold which has a lumen and in which a wire or a coil is inserted to impart a shape according to the lumen, can be used. FIGS. 2 to 5 show the coil portions 11 each having a primary shape that is linearly extended. This configuration is a form when it is held in a tube such as a catheter, and when it is not restrained by a tube wall of a catheter or the like, it can exhibit an indefinite shape or a secondary coil shape in which the coil portion 11 is further wound as shown in FIG. 1.

A secondary coil diameter of the coil portion 11 is appropriately determined according to an application site, for example, the size and inner diameter of an aneurysm, and is preferably 1 mm or larger, more preferably 1.5 mm or larger, and preferably 40 mm or smaller, more preferably 25 mm or smaller, even more preferably 20 mm or smaller.

The shape of the detachable portion 13 is a rod shape, and can be a columnar shape, a prismatic shape, or a combination thereof. An outer diameter of the detachable portion 13 varies depending on specific configurations of the pusher portion 30 and the coil portion 11 and is not restricted as long as the target coil portion 11 can be connected to the pusher portion 30 by an appropriate means. The detachable portion 13 preferably has an outer diameter of, for example, 0.05 mm or larger and 2.0 mm or smaller, and preferably has a length of 1.0 mm or longer and 10 mm or shorter.

A material of the detachable portion 13 is preferably those that do not adversely affect a living body and can be deformed or molten by a thermal, mechanical or electrical method, thereby separating the coil portion 11 from the pusher portion 30. Specifically, it is preferable that the detachable portion 13 contains a heat-melt material such as a polyvinyl alcohol polymer that is molten and cut by heating. The material of the detachable portion 13 is not limited to those, and a material which transforms by heating, such as a shape memory alloy and shape memory resin, for example, can be also used. Thereby, the coil portion 11 can be separated from the pusher portion 30 by a thermal operation.

The indwelling device 10 comprises a stretch-resistant member 20 disposed in the lumen of the coil portion 11. The stretch-resistant member 20 preferably has a linear body, and is disposed so as to be long in the longitudinal direction of the lumen of the coil portion 11. The stretch-resistant member 20 is preferably disposed in the state where the entire stretch-resistant member 20 extends in the longitudinal direction in the lumen of the coil portion 11.

A proximal end part of the stretch-resistant member 20 is anchored to the detachable portion 13. A distal end part of the stretch-resistant member 20 is preferably anchored to a distal part of the coil portion 11 and may be anchored to the head part 12. The stretch-resistant member 20 prevents the coil portion 11 from stretching more than necessary in a catheter or in a living body when the indwelling device 10 passes through the catheter and is delivered into the body. If the stretch-resistant member 20 is not disposed in the lumen of the coil portion 11, the coil portion 11 may stretch long and cannot be properly placed in a body, or the coil portion 11 may stretch completely to form a simple linear shape. It is preferable that the coil portion 11 is extendable in a range until the stretch-resistant member 20 is tensioned, that is, in a range until the stretch-resistant member 20 is elongated in a straight linear fashion.

The stretch-resistant member 20 is preferably separated from the pusher portion 30 while being attached to the coil portion 11 when the coil portion 11 is separated from the pusher portion 30 by cutting or the like the detachable portion 13. In particular, it is preferable that there is no change in the stretch-resistant member 20 and a structure for connecting the stretch-resistant member 20 to the detachable portion 13 in cutting the detachable portion 13.

Figure 2:
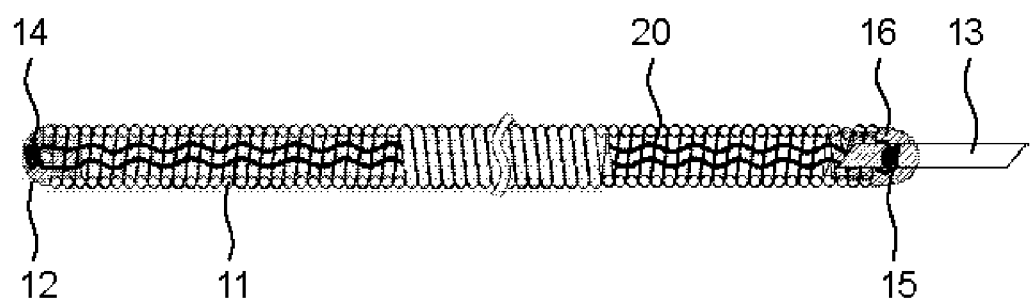
FIG. 2 shows an example of a distal part of an indwelling device for embolization of the present invention and represents a partial cross-sectional view seen from a lateral side of the distal part of the indwelling device.

A number of the stretch-resistant members 20 disposed in the lumen of the coil portion 11 is not particularly limited, and may be one or plural. In FIG. 2, two stretch-resistant members 20 are disposed in the coil portion 11. Alternatively, one stretch-resistant member 20 can be disposed in the coil portion 11 with being folded back. In this case, both ends of the stretch-resistant member 20 may be anchored to the detachable portion 13 and the folded part of the stretch-resistant member 20 may be anchored to the distal part of the coil portion 11.

The stretch-resistant member 20 can be composed of a single monofiber or a stranded wire thereof. Alternatively, the stretch-resistant member 20 can be composed of a metal wire of a platinum alloy such as platinum-tungsten, for example, in the same manner as the coil portion 11. In the case where the stretch-resistant member 20 is composed of a metal wire, there is a possibility that the stretch-resistant member 20 may be broken by metal fatigue when the coil portion 11 is repeatedly put in and out of a catheter in placing the coil portion 11 at an appropriate site in a body. In order to prevent this, the stretch-resistant member 20 can be composed of, for example, a metal material which is resistant to metal fatigue or a resin material which does not cause metal fatigue, such as polypropylene (PP).

Examples of a constituent material of a resin wire that can be used for the stretch-resistant member 20 include synthetic resins such as polyethylene, polypropylene, polyethylene terephthalate, polyamide, polyester, polylactic acid, polyglycolic acid, poly (lactic acid-glycolic acid) copolymer, polyhydroxybutyric acid, polyhydroxybutyrate valeric acid and a copolyester of 3-hydroxybutyric acid and 3-hydroxyhexanoic acid copolyester; polymers derived from a biodegradable polymer such as cellulose, polydioxanone, protein and vinyl polymer; and others. Among them, from the viewpoint of biocompatibility, the resin wire of the stretch-resistant member 20 is preferably made of polyethylene, polypropylene, nylon, polyester, polydioxanone, polytetrafluoroethylene, polyglycolic acid, polylactic acid, silk, or a composite material composed by any combination thereof.

A diameter of the resin wire is preferably 0.025 mm or larger and 0.125 mm or smaller. As a result, as is described below, knotting the stretch-resistant member 20 to the detachable portion 13 is facilitated.

The stretch-resistant member 20 may have a waveform with a certain wavelength. That is, the stretch-resistant member 20 may be formed in a waveform when viewed from the lateral side of the indwelling device 10. In placing the indwelling device 10 in a predetermined site such as an aneurysm, the long-shaped coil portion 11 is disposed in a small aneurysm, so that the coil portion 11 is bent in several places and packed in the aneurysm. In order to adapt for such deformation of the coil portion 11, the stretch-resistant member 20 preferably has a length that can follow the deformation or has a stretchability. For example, stretchability can be given by forming the stretch-resistant member 20 in a coil shape. Meanwhile, in the case where the stretch-resistant member 20 is extended too long, the coil portion 11 stretches and the operation for recovering the coil portion 11 to a catheter becomes difficult in recovering it for rearrangement.

As a method for anchoring the distal end part of the stretch-resistant member 20 to the distal part of the coil portion 11 or the head part 12 or a method for anchoring the proximal end part of the stretch-resistant member 20 to the detachable portion 13, adhesion using an adhesive, welding by including fusion or a inclusion, crimping such as mechanical caulking, physical connection, ligation, or other methods can be used, for example.

Figure 3:
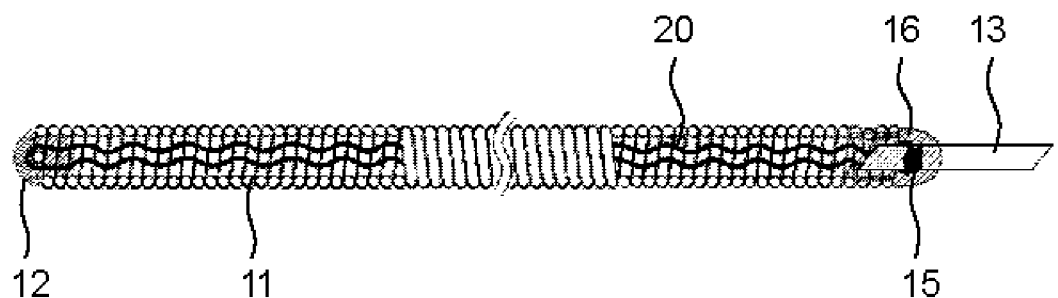
FIG. 3 shows another example of a distal part of an indwelling device for embolization of the present invention and represents a partial cross-sectional view seen from a lateral side of the distal part of the indwelling device.
Figure 4:
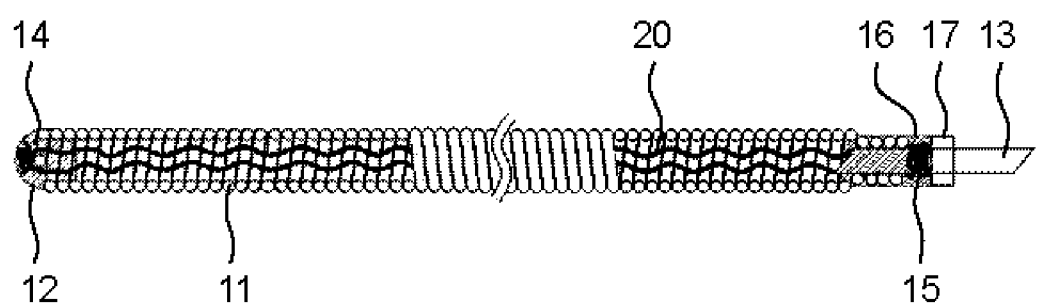
FIG. 4 shows another example of a distal part of an indwelling device for embolization of the present invention and represents a partial cross-sectional view seen from a lateral side of the distal part of the indwelling device.

The indwelling device 10 preferably has a fixing structure in which the stretch-resistant member 20 is knotted to the detachable portion 13. Thereby, anchoring strength between the stretch-resistant member 20 and the detachable portion 13 can be increased. In FIGS. 2 to 5, a knot 15 of which the stretch-resistant member 20 is knotted to the detachable portion 13 is formed as a fixing structure. The knot 15 is formed by knotting the proximal end part of the stretch-resistant member 20 to the detachable portion 13. The indwelling device 10 may also have a fixing structure in which the stretch-resistant member 20 is knotted to the distal part of the coil portion 11. In FIGS. 2 and 4, a knot 14 of which the stretch-resistant member 20 is knotted to the head part 12 of the coil portion 11 is formed as a fixing structure. The knot 14 is formed by knotting the distal end part of the stretch-resistant member 20 to the head part 12. The fixing structure may be reinforced by an adhesive or the like. That is, the fixing structure may include a cured adhesive. In FIGS. 2 to 5, the knot 15 is bonded with the adhesive 16, whereby the fixing structure is reinforced. Though it is not shown in the drawings, the knot 14 is also preferably is bonded with an adhesive, whereby the fixing structure is reinforced.

Figure 6:
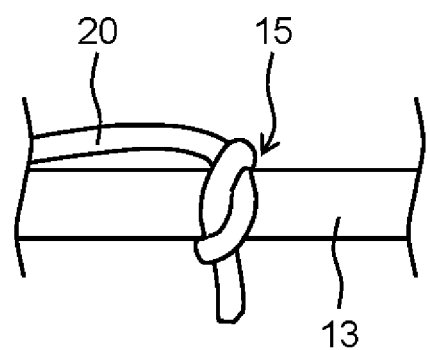
FIG. 6 shows an example of a fixing structure in which a stretch-resistant member is knotted to a detachable portion by a half-knot.

Various kinds of knotting methods can be adopted for the fixing structure of the stretch-resistant member 20, and its kind is not particularly limited. Examples of the kinds of the knot include a half-knot, a double knot, a bowline knot, a figure-eight knot, an S-shaped knot, a fisherman's knot, a granny knot, a slip knot and others. Among them, a half-knot is preferable since a smaller fixing structure can be formed. The half-knot is a knot obtained by forming a loop in a part of the stretch-resistant member 20, passing the proximal end part or the distal end part of the stretch-resistant member 20 once through the loop, and then tightening. FIG. 6 shows an example of the fixing structure in which the stretch-resistant member 20 is knotted to the detachable portion 13 by a half-knot.

The indwelling device 10 preferably comprises at least one half-knot disposed proximal to the proximal end of the lumen of the coil portion 11 as the fixing structure in which the stretch-resistant member 20 is knotted to the detachable portion 13. In the case of disposing two half-knots, it is preferable that, on the opposite side of the first half-knot in the detachable portion 13, the second half-knot is disposed, in order to make the fixing structure small.

Anchoring of the stretch-resistant member 20 to the distal part of the coil portion 11 may be made by, for example, disposing a structure formed by winding one round in a small spiral shape at the head part 12 of the coil portion 11 and hanging the stretch-resistant member 20 on this structure. As shown in FIG. 3, it is also possible that a middle part of the stretch-resistant member 20 is hanged on the structure formed at the head part 12 and the both ends of the stretch-resistant member 20 is knotted and anchored to the detachable portion 13. In this case, the stretch-resistant member 20 comes to be in a two-folded state in the lumen of the coil portion 11. That is, the stretch-resistant member 20 is disposed in the lumen of the coil portion 11 and is folded in a two-folded state at the distal part of the coil portion 11. Also in the case where the stretch-resistant member 20 is folded, one or a plurality of the stretch-resistant members 20 can be used.

Examples of a method for anchoring the stretch-resistant member 20 to the detachable portion 13 includes an embodiment that the stretch-resistant member 20 is knotted to the detachable portion 13 that protrudes proximally from the proximal end of the coil portion 11, that is, toward a right side in FIG. 2, by at least one half-knot to form a knot 15, whereby the proximal end part of the stretch-resistant member 20 is anchored to the detachable portion 13. A stronger anchoring strength can be realized by knotting the stretch-resistant member 20 twice or more as shown in FIG. 7, or by further bonding with an adhesive. However, when the stretch-resistant member 20 is knotted twice or more at the same position of the detachable portion 13, the knot 15 becomes larger, and in delivering the indwelling device 10 through a catheter into the body, friction between the indwelling device and an inner wall of the catheter or an inner wall of a blood vessel increases, whereby the indwelling device 10 may be damaged or the blood vessel may be ruptured. Therefore, in the case where the stretch-resistant member 20 is knotted to the detachable portion 13 twice or more, it is preferably knotted at different positions on the detachable portion 13. That is, it is preferable that the fixing structure includes a plurality of half-knots located at different positions. The knot 15 of the stretch-resistant member 20 may be disposed in the lumen of the coil portion 11 or may be disposed out of the lumen of the coil portion 11.

The distal part of the detachable portion 13 is preferably disposed within the lumen of the coil portion 11. Thereby, the fixing structure can be strengthened more. In the case where the distal part of the detachable portion 13 is disposed in the lumen of the coil portion 11, the knot 15 of the stretch-resistant member 20 may be arranged at a part of the detachable portion 13 that is positioned in the lumen of the coil portion 11, or may be arranged at a part of the detachable portion 13 that is positioned out of the coil portion 11. In the case of disposing a plurality of the knots 15, one or some of the plurality of knots 15 may be arranged in the lumen of the coil portion 11 and the others of those may be arranged out of the coil portion 11. In addition, one knot 15 may be arranged so as to extend from inside the lumen of the coil portion 11 to out of that. Preferably, the distal part of the detachable portion 13 is disposed inside the coil portion 11 and the knot 15 of the stretch-resistant member 20 is disposed out of the coil portion 11. In the case where the fixing structure of the knot 15 is reinforced with an adhesive, a cured adhesive is preferably disposed to extend from the proximal part of the coil portion 11 to the distal part of the detachable portion 13.

As the adhesive forming the fixing structure, those having low biotoxicity and biocompatibility are preferable, and an ultraviolet curable adhesive, a thermosetting adhesive or a moisture curable adhesive can be used. As the adhesive, a resin having similar properties can be used. Accordingly, the fixing structure can include a cured resin and the stretch-resistant member. Since the knot is fixed with an adhesive, viscosity of the adhesive is preferably 10 mPa·s or more and 2000 mPa·s or less. Examples of the adhesive include polyurethane adhesives and cyanoacrylate adhesives.

The ultraviolet curable adhesive is cured in a short time by irradiating ultraviolet rays, and examples thereof include acrylic resin adhesives and epoxy adhesives. The thermosetting adhesive is cured by activating a curing agent contained in the resin with heating, and examples thereof include epoxy resin adhesives and acrylic resin adhesives. The moisture curable adhesive is cured by reacting with moisture in air, and examples thereof include cyanoacrylate adhesives and silicone rubber adhesives.

In the case where the knot 15 is reinforced with the adhesive 16, the diameter of the knot 15 fixed with the adhesive 16 is preferably smaller than the outer diameter of the coil portion 11.

From the viewpoint of further strengthening the fixing structure of knotting the stretch-resistant member 20, the detachable portion 13 may have one or more grooves formed on the surface thereof. The groove on the detachable portion 13 may extend along the longitudinal direction of the indwelling device 10 or may extend along a direction perpendicular to the longitudinal direction, for example, a circumference direction of the coil portion 11. In the case where the groove on the detachable portion 13 is arranged so as to extend in a direction perpendicular to the longitudinal direction, the fixing structure in which the stretch-resistant member 20 is knotted can be disposed at a part where the groove is formed. Thereby, the fixing structure can be strengthened more. In addition, regardless of the direction of the groove, the fixing structure can be strengthened by the adhesive flowing into the groove.

In the case where the distal part of the detachable portion 13 is disposed in the lumen of the coil portion 11, it is preferable that the adhesive stays in a part where the groove is formed on the detachable portion 13 that is located inside the coil portion 11. That is, it is preferable that the cured adhesive is disposed at a part where the groove is formed on the detachable portion 13 that is located inside the coil portion 11. As a result, cutting of the detachable portion 13 can be made easier. In the case where an insulating portion 17, which is described below, is disposed, as the cured adhesive is disposed distal to the proximal end of the insulating portion 17 which disposed on the proximal side of the coil portion 11, cutting of the detachable portion 13 can be made further easier. From the viewpoint of facilitating cutting of the detachable portion 13, it is preferable that the cured adhesive is essentially disposed at a part where the groove is formed on the detachable portion 13 that is located inside the coil portion 11. In this case, the cured adhesive may be disposed inside the coil portion 11 distal to the detachable portion 13 or may be disposed at a part other than the groove on the detachable portion 13 that is located inside the coil portion 11. The detachable portion 13 preferably has a part in which an adhesive does not exist and which is formed so as to surround the detachable portion 13 along the circumferential direction thereof, whereby cutting of the detachable portion 13 can be made further easier.

Figure 5:
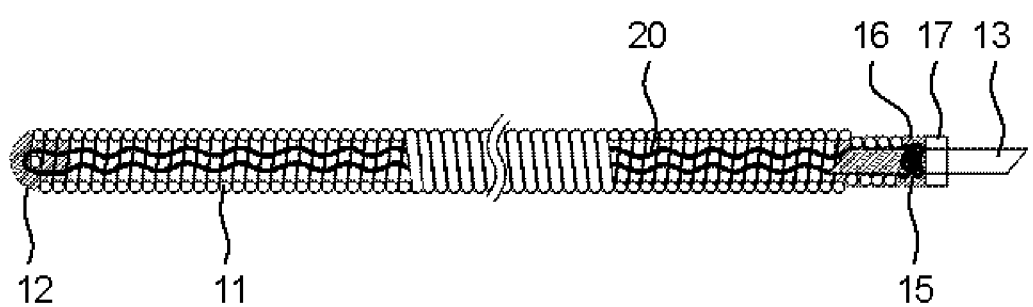
FIG. 5 shows another example of a distal part of an indwelling device for embolization of the present invention and represents a partial cross-sectional view seen from a lateral side of the distal part of the indwelling device.

As shown in FIGS. 4 and 5, the inner diameter of the proximal end part of the coil portion 11 is preferably smaller than the inner diameter of the distal part of the coil portion 11. A part where the diameter of the proximal end part of the coil portion 11 is reduced in this manner is referred to as a small diameter portion. By providing the small diameter portion, the knot 15 is easily disposed out of the coil portion 11. In addition, since the distance between the coil portion 11 and the stretch-resistant member 20 can be set closer on the proximal end part of the coil portion 11, adhesion of the stretch-resistant member 20 to the coil portion 11 can be strengthened more.

The small diameter portion is preferably disposed at least at the proximal end of the coil portion 11, and may be disposed on the distal side by about 1 to 10 rounds of the wire from the proximal end. The small diameter portion is preferably disposed at a position in the range of 10 or less rounds of the wire from the proximal end of the coil portion 11, more preferably in the range of 6 rounds or less rounds, and even more preferably in the range of 4 rounds or less rounds. In the small diameter portion, the coil portion 11 is preferably reduced in diameter so that the inner diameter thereof is reduced to about the outer diameter of the detachable portion 13. The inner diameter of the small diameter portion is preferably 95% or less of the inner diameter of the distal part of the coil portion 11. The small diameter portion may be disposed so as to bite into the detachable portion 13.

As shown in FIGS. 4 and 5, an insulating portion 17 can be disposed on the detachable portion 13 proximal to the fixing structure. Thereby, a tip of the pusher portion 30 can be prevented from electrically connecting to the coil portion 11. This is because when the tip of the pusher portion 30 and the coil portion 11 are electrically connected to each other at a bending part of a blood vessel or the like, a short circuit may occur and the coil portion 11 may be likely not be detached therefrom.

A material of the insulating portion 17 is not particularly limited as long as it is non-conductive or insulating, and is preferably biocompatible. The material of the insulating portion 17 is preferably those that do not substantially swell with water, and specific examples thereof include a cured adhesive of a cyanoacrylate adhesive, an epoxy adhesive or the like. In addition to those, the insulating portion 17 can be made of various biocompatible polymer materials, and for example, a thermoplastic resin such as polyethylene, polypropylene and polyethylene terephthalate (PET), a thermosetting resin such as polytetrafluoroethylene (PTFE), polyamide, polyimide, silicone rubber and latex rubber, or a hydrophilic resin such as polyvinyl alcohol can be used. For these resins, one kind thereof may be used or two or more kinds thereof may be used in combination. Particularly, the insulating portion 17 is preferably made of at least one polymer material selected from the group consisting of polyethylene terephthalate (PET), polytetrafluoroethylene (PTFE), polyvinyl alcohol (PVA) and cyanoacrylate.

The insulating portion 17 has a ring shape. By passing the ring-shaped insulating portion 17 through the rod-shaped separating portion 13, the insulating portion 17 can be disposed on the separating portion 13. A cross-sectional shape of the ring-shaped insulating portion 17 is not limited to a circle, and may be an ellipse or a polygon such as a quadrangle and a triangle. The insulating portion 17 preferably has a length in the longitudinal direction of 0.15 mm or longer and 0.20 mm or shorter. When the length of the insulating portion 17 is too long, the detachable portion 13 may become harder, and when it is too short, an adhesive or the like may flow into a part to be heated of the detachable portion 13 and the detachable portion 13 may be difficult to be separated.

Next, a method for manufacturing the indwelling device is explained. A method for manufacturing an indwelling device of the present invention comprises: disposing a stretch-resistant member inside a coil portion (that is referred to as an "stretch-resistant member disposing step"); inserting a detachable portion into a proximal end part of the coil portion (that is referred to as a "detachable portion insertion step"); forming a fixing structure by knotting the stretch-resistant member to the detachable portion (that is referred to as a "fixing structure forming step"); injecting an adhesive into the fixing structure (that is referred to as a "adhesive injection step); and curing the adhesive (that is referred to as a "adhesive curing step"). The order of conducting these steps is not particularly limited except that the adhesive injection step is conducted after the fixing structure forming step and the adhesive curing step is further conducted after the adhesive injection step. In addition, the detachable portion insertion step is preferably conducted after the stretch-resistant member disposing step.

In the stretch-resistant member disposing step, the stretch-resistant member is disposed in the lumen of the coil portion. The stretch-resistant member is inserted from one end of the coil portion, that is, a proximal end or a distal end thereof. In the case where a structure for hanging or anchoring the stretch-resistant member is provided at the head of the distal end part of the coil portion, the stretch-resistant member is preferably inserted from the proximal end of the coil portion. In the stretch-resistant member disposing step, it is preferable that a distal part of the stretch-resistant member is placed in the coil portion and a proximal end part of that is placed out of the coil portion. Thereby, in the case where the fixing structure forming step is conducted after the stretch-resistant member disposing step, knotting of the stretch-resistant member to the detachable portion is facilitated in the fixing structure forming step. In the case where the fixing structure forming step is conducted before the stretch-resistant member disposing step, the proximal end part of the stretch-resistant member may be placed in the lumen of the coil portion or may be placed out of the coil portion.

In the detachable portion insertion step, a rod-shaped detachable portion is inserted from the proximal end of the coil portion and placed at a proximal end part of the coil portion. In the detachable portion insertion step, it is preferable to insert the detachable portion into the proximal end of the coil portion so that a proximal part of the detachable portion protrude proximally from the proximal end of the coil portion. Thereby, it becomes possible to attach the proximal part of the detachable portion to a pusher portion. Alternatively, in the detachable portion insertion step, the detachable portion may be inserted into the proximal end part of the coil portion with the proximal part of the detachable portion attached to the pusher portion. In the case where the fixing structure forming step is conducted after the detachable portion insertion step, when the proximal part of the detachable portion protrudes proximally from the proximal end of the coil portion, knotting of the stretch-resistant member to the detachable portion is facilitated in the fixing structure forming step.

In the fixing structure forming step, a fixing structure is formed by knotting the stretch-resistant member to the rod-shaped detachable portion. In the fixing structure forming step, a half-knot is made by, for example, forming a loop by the proximal part of the stretch-resistant member on the proximal side of the proximal end of the coil portion, passing the proximal end part of the stretch-resistant member through the loop once and then tightening. Furthermore, it is preferable to make another half-knot on the opposite side of the first half-knot on the detachable portion.

The fixing structure forming step may be conducted before or after the stretch-resistant member disposing step, or may be conducted before or after the detachable portion insertion step. For example, after forming the fixing structure by knotting the stretch-resistant member to the detachable portion, the stretch-resistant member may be disposed inside the coil portion as well as the detachable portion may be inserted into the proximal end part of the coil portion; after forming the fixing structure by knotting the proximal end part of the stretch-resistant member to the detachable portion in the state where the distal part of the stretch-resistant member is disposed inside the coil portion, the detachable portion may be inserted into the proximal end part of the coil portion; or in the state where the distal part of the stretch-resistant member is disposed inside the coil portion, the proximal end part of that is disposed out of the coil portion and the detachable portion is inserted into the proximal end part of the coil portion, the proximal end part of the stretch-resistant member may be knotted to the detachable portion to form the fixing structure.

In the adhesive injection step, an adhesive is injected so that the adhesive contacts the knot formed in the fixing structure formation step. The adhesive only needs to come into contact with at least the knot and the detachable portion, and further, the adhesive is preferably injected into the lumen of the coil portion. The knot may be located in the lumen of the coil portion or may be located out of the lumen. In the case where the adhesive is injected further into the lumen of the coil portion, the adhesive is preferably injected so as to extend from the proximal part of the coil portion to the distal part of the detachable portion. That is, it is preferable that the knot, the detachable portion and the lumen of the coil portion are in contact with the adhesive. The adhesive injected into the lumen of the coil portion preferably does not reach the outside of the coil portion through the gap between the metal wires constituting the coil portion.

In the adhesive curing step, the adhesive applied in the adhesive injection step is cured. For example, in the case of using an ultraviolet curable adhesive, it is preferable to uniformly irradiate the applied adhesive with ultraviolet rays using a UV lamp to cure the adhesive. In the case of using a thermosetting adhesive, it is preferable to heat the applied adhesive with a heater or the like to cure the adhesive. In the case of using a moisture curable adhesive, the adhesive can be cured by leaving it in air with humidity adjusted as necessary.

The adhesive curing step may be conducted immediately after the adhesive injecting step, or the stretch-resistant member disposing step and/or the detachable portion insertion step may be conducted after the adhesive injecting step, and then the adhesive curing step may be conducted. However, the adhesive curing step is preferably conducted immediately after the adhesive injection step.

A step of reducing a diameter of the proximal end part of the coil portion (that is referred to as a "coil contraction step") may be provided after the stretch-resistant member disposing step. By conducting the coil contraction step, a small diameter portion can be disposed at the proximal end part of the coil portion. Examples of a method of reducing the diameter of the proximal end part of the coil portion include, for example, a method of pulling a metal wire at the proximal end of the coil portion to the proximal side to reduce the diameter of the proximal end part thereof, a method of placing a core material which is smaller than the lumen of the coil portion at the proximal end part of the coil portion, tightening a helical winding of a metal wire at the proximal end part of the coil portion, and forming a coil having a smaller diameter on the core material, and others. The coil contraction step may be conducted before or after the detachable portion insertion step, or may be conducted before or after the fixing structure forming step.

This application claims priority to Japanese Patent Application No. 2017-174746, filed on Sep. 12, 2017. All of the contents of the Japanese Patent Application No. 2017-174746, filed on Sep. 12, 2017, are incorporated by reference herein.

EXAMPLES

Hereinafter, examples performed for confirming effects of the indwelling device of the present invention are explained.

Example 1

Using a platinum-tungsten alloy wire having a wire diameter of 70 μm, a coil portion having a coil diameter of 360 μM and a coil length of 10 mm was prepared. At a distal end part of the coil portion, a head structure formed by winding one round in a small spiral shape was made. A stretch-resistant member prepared by folding a polypropylene resin (hereinafter referred to as "PP") wire was inserted from a proximal end of the coil portion with the folded part being at the head to reach a distal end part of the coil portion, and the folded part was hanged on the head structure of the coil portion. The folded part of the hanged PP wire and the head structure of the coil portion were fixed with an ethyl cyanoacrylate adhesive to form a substantially hemispherical round head part. A detachable portion was inserted into a proximal end part of the coil portion, and the proximal end of the folded PP wire, that is, both ends of the PP wire, was knotted on the detachable portion, which protruded from the proximal end of the coil portion, at two different positions with half-knots. A UV curable adhesive was injected into the knots and the lumen of the coil portion, thereby fixing the coil portion, the knots and the detachable portion. The resultant was referred to as an "indwelling device 1".

Example 2

In the same manner as Example 1, a PP wire was hanged on the head structure of the coil portion, the head was formed, and then a detachable portion was inserted into the proximal end part of the coil portion and both ends of the PP wire, that is, the proximal end of the folded PP wire, was knotted on the detachable portion, which protruded from the proximal end of the coil portion, at one position with a half-knot. A UV curable adhesive was injected into the knot and the lumen of the coil portion, thereby fixing the coil portion, the knot and the detachable portion. The resultant was referred to as an "indwelling device 2".

Comparative Example

In the same manner as Example 1, a PP wire was hanged on the head structure of the coil portion, the head was formed, and then a detachable portion was inserted into the proximal end part of the coil portion. An adhesive was injected into a contact part between the detachable portion and the proximal end part of the coil portion, thereby fixing the coil portion, the PP wire and the detachable portion. The resultant was referred to as a "comparison indwelling device".

For each of the indwelling devices 1 and 2 and the comparative indwelling device manufactured as described above, anchoring strength of the PP wire in a dry state and a swollen state was evaluated. The anchoring strength was evaluated by measuring breaking strength of the adhesion part of the indwelling device in the longitudinal direction.

Table 1 shows the measurement results of the breaking strength of the adhesion part of the indwelling device in the longitudinal direction. The breaking strength was determined by chucking the detachable portion of the indwelling device and the head part of the coil portion at ordinary temperature and conducting a tensile test under a condition of a load cell scale of 2.5NFS and a tensile speed of 50 mm/min, using a tensile compression tester "Strograph EIII" (manufactured by Toyo Seiki Seisakusho Co., Ltd.).

TABLE 1

| | Detachable portion in a dry state | | | | |
|---|---|---|---|---|---|
| | Number of knot | Sample No. | | | |
| | | 1 | 2 | 3 | Average |
| Indwelling device 1 (invention) | 2 | 0.76 | 0.90 | 0.69 | 0.78 |
| Indwelling device 2 (invention) | 1 | 0.66 | 0.93 | 0.73 | 0.77 |
| Comparative Indwelling device | 0 | 0.47 | 0.14 | 0.29 | 0.30 |

| | Detachable portion in a swollen state | | | | |
|---|---|---|---|---|---|
| | Number of knot | Sample No. | | | |
| | | 4 | 5 | 6 | Average |
| Indwelling device 1 (invention) | 2 | 1.34 | 1.24 | 0.95 | 1.18 |
| Indwelling device 2 (invention) | 1 | 0.72 | 0.84 | 0.88 | 0.81 |
| Comparative Indwelling device | 0 | 0.44 | 0.65 | 0.50 | 0.53 |

From the results shown in Table 1, it is understood that the adhesion parts of the indwelling devices 1 and 2 have a higher breaking strength than that of the comparative indwelling device and have a sufficiently high anchoring strength. Therefore, the indwelling devices 1 and 2 can obtain high safety when conducting indwelling operation.

REFERENCE SIGNS LIST

10: an indwelling device for embolization
11: a coil portion
12: a head part
13: a detachable portion
14: a knot
15: a knot
16: an adhesive
17: an insulating portion
20: a stretch-resistant member
30: a pusher portion

The invention claimed is:

1. An indwelling device for embolization comprising;
a coil portion having a proximal end and a distal end and having a lumen extending in a longitudinal direction;
a stretch-resistant member disposed in the lumen and extending from the proximal end part to the distal end part of the coil portion;
a rod-shaped detachable portion having a rod part extending in the longitudinal direction, an end part of the rod-shaped detachable portion disposed in the lumen of the proximal end part of the coil portion so that another end part of the rod-shaped detachable portion proximally extends from the proximal end part of the coil portion, and
a fixing structure including a knot in which the stretch-resistant member is knotted to the rod part of the detachable portion, the knot disposed on the rod part of the detachable portion.

2. The indwelling device for embolization according to claim 1, wherein
an insulating portion is disposed on the detachable portion and proximal to the fixing structure.

3. The indwelling device for embolization according to claim 1, wherein
the coil portions has a small diameter portion at a proximal end part, the small diameter portion has an inner diameter, which is smaller than an inner diameter of a distal part of the coil portion.

4. The indwelling device for embolization according to claim 1, wherein
the knot is at least one half-knot disposed proximal to a proximal end of the lumen of the coil portion.

5. The indwelling device for embolization according to claim 1, wherein
the knot is a plurality of half-knots located at different positions on the detachable portion.

6. The indwelling device for embolization according to claim 1, wherein
the stretch-resistant member is folded in a two-folded state at a distal part of the coil portion.

7. The indwelling device for embolization according to claim 1, wherein
the fixing structure includes a cured adhesive attached to a portion where the stretch-resistant member is knotted to the detachable portion, and
an adhesive to form the cured adhesive is selected from a group consisting of an ultraviolet curable adhesive, a thermosetting adhesive and a moisture curable adhesive each having a viscosity of 10 mPa·s to 2000 mPa·s.

8. The indwelling device for embolization according to claim 7, wherein
the cured adhesive is disposed to extend from a proximal part of the coil portion to a distal part of the detachable portion.

9. The indwelling device for embolization according to claim 1, wherein
the knot of the stretch-resistant member is disposed out of the lumen of the coil portion.

10. The indwelling device for embolization according to claim 1, wherein
the detachable portion comprises a heat-melt material.

11. The indwelling device for embolization according to claim 1, further comprises a pusher portion, wherein
the coil portion, the detachable portion and the pusher portion are disposed in this order from a distal side of the indwelling device, and
the coil portion and the pusher portion are connected to each other via the detachable portion.

12. The indwelling device for embolization according to claim 1, wherein
the stretch-resistant member is a linear member, and
one end of the stretch-resistant member is fixed at a distal portion of the coil portion, and another end of the stretch-resistant member is knotted to the detachable portion.

13. The indwelling device for embolization according to claim 1, wherein a distal end of the detachable portion is disposed inside the coil portion, and the knot of the stretch-resistant member is disposed out of the lumen of the coil portion.

14. A method for manufacturing an indwelling device for embolization comprising:
   disposing a stretch-resistant member inside a coil portion which extends in a longitudinal direction;
   inserting a detachable portion into a proximal end part of the coil portion, wherein the detachable portion has a rod part extending in the longitudinal direction;
   forming a fixing structure by knotting the stretch-resistant member to the rod part of the detachable portion to fix the stretch-resistant member to the detachable portion, whereby a knot is formed on the rod part of the detachable portion;
   applying an adhesive to the fixing structure; and
   curing the adhesive.

15. The method for manufacturing an indwelling device for embolization according to claim 14, further comprising reducing an inner diameter of a proximal end of the coil portion after the step of disposing the stretch-resistant member inside the coil portion.

16. The method for manufacturing an indwelling device for embolization according to claim 14, wherein
   the knot is at least one half-knot disposed proximal to a proximal end of the lumen of the coil portion.

17. The method for manufacturing an indwelling device for embolization according to claim 14, wherein
   the knot of the stretch-resistant member is disposed out of the lumen of the coil portion.

18. The method for manufacturing an indwelling device for embolization according to claim 14, wherein
   a distal end of the detachable portion is disposed inside the coil portion, and
   the knot of the stretch-resistant member is disposed out of the lumen of the coil portion.

* * * * *